(12) United States Patent
Ling

(10) Patent No.: US 7,678,562 B2
(45) Date of Patent: Mar. 16, 2010

(54) ADDRESSABLE NANOPORES AND MICROPORES INCLUDING METHODS FOR MAKING AND USING SAME

(75) Inventor: Xinsheng Sean Ling, East Greenwich, RI (US)

(73) Assignee: Brown University, Providence, RI (US)

( * ) Notice: Subject to any disclaimer, the term of this patent is extended or adjusted under 35 U.S.C. 154(b) by 1630 days.

(21) Appl. No.: 10/788,539

(22) Filed: Feb. 27, 2004

(65) Prior Publication Data
US 2005/0127035 A1 Jun. 16, 2005

Related U.S. Application Data

(60) Provisional application No. 60/451,088, filed on Feb. 28, 2003, provisional application No. 60/507,354, filed on Sep. 29, 2003, provisional application No. 60/512,140, filed on Oct. 16, 2003.

(51) Int. Cl.
*C12M 1/00* (2006.01)
*B29C 37/02* (2006.01)
*B31D 3/00* (2006.01)

(52) U.S. Cl. .................. 435/283.1; 216/56; 422/82.01; 422/82.05; 435/6; 435/288.2; 435/288.5; 977/720; 977/932

(58) Field of Classification Search ........... 345/87–100, 345/204–214; 324/770, 522–528
See application file for complete search history.

(56) References Cited

U.S. PATENT DOCUMENTS

| | | | | |
|---|---|---|---|---|
| 5,314,829 A | * | 5/1994 | Coles | .................. 436/165 |
| 5,795,782 A | | 8/1998 | Church et al. | |
| 6,013,923 A | * | 1/2000 | Huang | .................. 257/59 |
| 6,020,599 A | | 2/2000 | Yeo | |
| 6,025,891 A | | 2/2000 | Kim | |
| 6,084,648 A | | 7/2000 | Yeo | |
| 6,100,949 A | | 8/2000 | Kim | |
| 6,128,051 A | | 10/2000 | Kim et al. | |
| 6,392,719 B2 | | 5/2002 | Kim | |
| 6,400,425 B1 | | 6/2002 | Kim et al. | |

(Continued)

OTHER PUBLICATIONS

Kuo et al., "Hybrid three-dimensional nanofluidic/microfluidic devices using molecular gates", Sensors and Actuators A, vol. 102 (Oct. 2002):223-233.

(Continued)

*Primary Examiner*—B J Forman
*Assistant Examiner*—Narayan K Bhat
(74) *Attorney, Agent, or Firm*—Wilmer Cutler Pickering Hale and Dorr LLP

(57) ABSTRACT

Featured are devices and systems embodying one or more electrically-addressable-solid-state nanopores useful for sensing and/or characterizing single macromolecules as well as sequencing DNA or RNA. In one aspect of the present invention, there is featured a linear or 2-D electrically-addressable array of nanopores, where the nanopores are located at points of intersections between V-shaped grooves formed in an upper surface of the insulating member and a V-shaped groove formed in a lower surface of the insulating member. In another aspect of the present invention the solid-state nanopore of the present invention the width and/or length of the nanopore is defined or established by sharp edges of cleaved crystals that are maintained in fixed relation during the formation of the insulating member including the nanopore.

14 Claims, 7 Drawing Sheets

U.S. PATENT DOCUMENTS

| | | | |
|---|---|---|---|
| 6,428,959 B1 * | 8/2002 | Deamer | 435/6 |
| 6,464,842 B1 * | 10/2002 | Golovchenko et al. | 204/192.13 |
| 6,503,409 B1 | 1/2003 | Fleming | |
| 6,537,755 B1 | 3/2003 | Drmanac | |
| 6,566,902 B2 * | 5/2003 | Kwon et al. | 324/770 |
| 6,784,862 B2 * | 8/2004 | Kodate et al. | 345/92 |
| 6,839,121 B2 * | 1/2005 | Kim et al. | 324/770 |
| 2002/0058279 A1 * | 5/2002 | Fritsch et al. | 435/6 |
| 2002/0140650 A1 * | 10/2002 | Kai et al. | 345/87 |
| 2003/0210359 A1 * | 11/2003 | Lee et al. | 349/43 |
| 2006/0077162 A1 * | 4/2006 | Chou et al. | 345/92 |

OTHER PUBLICATIONS

Li et al., "Lon-beam sculpting at nanometre length scales", Nature, vol. 412 (Jul. 2001): 166-169.

Storm et al., "Fabrication of solid-state nanopores with single-nanometre precision", Nature Materials, vol. 2 (Aug. 2003):537-540.

* cited by examiner

ADDRESSABLE NANOPORES AND MICROPORES INCLUDING METHODS FOR MAKING AND USING SAME

CROSS-REFERENCE TO RELATED APPLICATIONS

This application is related to and claims priority from earlier filed Provisional Patent Application No. 60/451,088, filed on Feb. 28, 2003; Provisional Patent Application No. 60/507,354, filed on Sep. 29, 2003; and Provisional Patent Application No. 60/512,140, filed on Oct. 16, 2003.

BACKGROUND OF THE INVENTION

The present invention relates generally to nanopore and micropore devices and methods for their manufacture and use. More particularly the present invention relates to nanopore and micropore devices used for detecting, and characterizing biomolecules, as well as sequencing nucleic acids, and new methods for fabrication and application thereof.

Nanopores and micropores are structures that are useful and implemented for a wide range of applications. Nanopores are holes with diameters in the range of 100 nm to 1 nm in a membrane or solid media. Micropores refer to holes with diameters ranging from 100 nm to 100 µm. For nanopores, many applications have been contemplated including rapid detection and characterization of biological agents, and DNA sequencing. Micropores are already widely used as a mechanism for separating cells.

For the applications of DNA sequencing, two prior-art methods have been proposed using nanopores. U.S. Pat. No. 5,795,782, issued to Church et al. discloses a method of reading DNA sequence by detecting the ionic current variations as a single-stranded DNA molecule moving through the nanopore under a bias voltage. Another method for DNA sequencing using nanopores was discussed in U.S. Pat. No. 6,537,755, issued to Drmanac. Drmanac proposes to use nanopores to detect the DNA hybridization probes (oligonucleotides) on a DNA molecule and recover the DNA sequence information using the method of Sequencing-By-Hybridization (SBH).

Other applications using nanopores have been discussed widely in literature, including real-time monitoring of cell activities and detection of biological agents in biodefense. For many of these important applications, it is highly desirable to develop nanopore devices using solid-state materials. Here solid-state materials are broadly defined including high-density materials such as silicon oxides and nitrides, and polymeric materials such as hard plastics, as they are naturally insulating or can be insulated by adding a surface layer or making the surface insulating, e.g. by oxidization.

A well-known technique for producing nanoscale holes in solid-state materials uses high-energy particles to create damage tracks. The tracks become nanoscale holes when etched. Because a freestanding nanometer-thick film is mechanically unstable, the nanopores produced by this technique often have length on the order of a micrometer or more and are typically limited by the thickness of the starting film. For example, such long nanopores (also called nano-capillaries) were used by Bohn et al., in US Patent Publication No. 2003/0136679 and Kuo et al., in "*Hybrid three-dimensional nanofluidic/microfluidic devices using molecular gates*", Sensors and Actuators A, vol. 102 (October 2002): 223-233. Such long nanopores are not suitable for many applications such as DNA sequencing as currently discussed. Recent efforts in this field have been focused on developing new techniques for fabricating short nanopores having a pore length that is less than 20 nm.

U.S. Pat. No. 6,464,842, issued to Golovchenko et al. proposed a film-thinning technique. In the disclosed method, a shallow cavity is first created on one side of a membrane; the membrane is then thinned down from the opposite side slowly using a low-energy ion beam. Utilizing an active feedback loop to control the application of the low-energy ion beam, one can stop the thinning process as soon as a pore is opened at the cavity. This technique has been further developed into a nanoscale "sculpting" approach, [see Li et al., "*Ion-beam sculpting at nanometer length scales*", Nature, vol. 412 (July 2001): 166-169]. The main drawback of this approach is that highly specialized and expensive ion-beam instrumentation is needed.

In U.S. Pat. No. 6,503,409, Fleming proposes a method of making a nanopore (or nano-aperture) using silicon technology. In Fleming's approach, a nanopore is formed at the crossing point of two nanoslits. The nanoslits are fabricated by etching away a thin (2-5 nm) layer of sacrificial material. Because the pore size is controlled by the thickness of the sacrificial layer, the channel connecting to the pore is also of 2-5 nm in thickness. This feature is highly undesirable since the DNA molecules will be less likely to access the pore due to the large penalty in free energy (known as the entropic barrier) they have to overcome to reach the pore.

To take advantage of the silicon technology while avoiding the limit of the Fleming approach, Storm et al. [Storm et al., "*Fabrication of solid-state nanopores with single-nanometer precision*", Nature Materials, vol. 2 (August 2003): 537-540.] proposed a different method. Storm et al. used standard electron-beam lithography to create a 100 nm etch mask on the surface of a silicon membrane. When this mask is exposed to KOH solutions, an inverse pyramid feature is developed due to the anisotropy of the etching rate along different crystalline axes. Storm et al. showed that one can simply control the etching time so that a pore of 20 nm is opened on the opposite side of the etch mask. After oxidization, the silicon around the pore opening is turned into silicon oxide ($SiO_2$). In the next step the $SiO_2$ material around the pore is fluidized using a high-energy electron beam, such that the surface tension of the fluidized $SiO_2$ pulls the material into the empty space thereby reducing the pore size. This technique has been shown to have great reliability in producing nanopores with diameters ranging from 1-20 nm. The pores can also be completely closed off using the same technique.

There are at least two major limitations in all of the above discussed techniques related to nanopore fabrication. The first is that all of the above techniques only produce individual pores. A single nanopore in a membrane will have very low throughput in molecule sensing operations. Accordingly, it is highly desirable to have an array of nanopores on the same membrane. However, a device using a membrane with many parallel pores will not be useful, since one cannot determine which pore a DNA is moving through. Second, all of the above techniques produce nanopores having pore length on the order of 10 nm or more.

In order to make the nanopores useful for practical applications, one needs to create a high-throughput device such as an array of nanopores wherein each pore in the array is independently electrically addressable. It would be desirable to provide a device and method that yields a linear array of nanopores or two-dimensional array of nanopores. It also would be particularly desirable to provide such linear and two-dimensional nanopore arrays that are electrically addressable. It would further be desirable to provide a new nanopore that can be formed using synthetic material and a method for using and making such a nanopore. It also would be desirable to provide a nanopore or an array of nanopores each with a length of less than 10 nm. It would be highly desirable to have simplified processes for fabricating nanopores and related fluidic systems at low cost.

BRIEF SUMMARY OF THE INVENTION

In this regard, the present invention provides devices and systems that embody one or more addressable solid-state nanopores that are fabricated utilizing low-cost processes, which can be used to sense and/or characterize single macromolecules as well as sequencing DNA or RNA. Such devices and systems have a wide range of applications in molecular biology and medical science. In addition to being useful for rapid DNA sequencing, the devices and systems of the present invention can be used in a variety of applications involving, but not limited to, single-molecule biophysics, molecular biology, and biochemistry. For example, nanopore devices and systems of the present invention are contemplated for use as a molecular comb to probe the secondary structure of RNA molecules, for use in detecting biological warfare agents, contaminants and pollutants in air and/or water.

According to one aspect of the present invention, there is featured an electrically-addressable nanopore array that is configured and arranged so as to allow high throughput analyses of biomolecules as well as sequencing DNA. In a preferred embodiment, the electrically-addressable nanopore array includes a linear or one-dimensional array of nanopores formed by crossing two sets of V-shaped grooves on the opposing sides of an insulating material layer. The V-grooves are produced by any of the known methods, including etching, machining, molding, or extrusion. In another embodiment, the nanopore array includes a two-dimensional array of nanopores. In other embodiments, the two-dimensional array is in the form of a plurality of linear arrays. In further embodiments the linear and two dimensional nanopore arrays are formed and arranged in the insulating material so each of the nanopores can be addressed independently using an electric current provided by, for example, a standard patch-clamp method.

In particular embodiments, the electrically addressable nanopore array includes an insulating material layer. The insulating material layer is configured and arranged so as to have one or more V-grooves extending lengthwise in a first direction in a first surface thereof and being parallel to each other. The insulating material layer is configured and arranged so as to have a V-groove also is formed in the insulating material layer second surface that extends lengthwise in a second direction in a second surface thereof, where the first and second surfaces are opposed to each other. Also, the second direction is at an angle with respect to the first direction, more particularly the first and second directions are orthogonal to each other or at about a 90° angle with respect to each other.

The V-grooves are also formed in each of the first and second surfaces so as to extend downwardly from one surface to the other surface, so that at the region of intersection between each of the V-grooves in the first surface and the V-groove in the second surface there is formed an opening that forms a nanopore. In this way a plurality of nanopores are formed in a linear or one-dimensional array in the insulating material at the intersection of each of the plurality of V-grooves in the first surface and the V-groove formed in the second surface.

As indicated above, in further embodiments the insulating material layer is configured and arranged so as to have a plurality of V-grooves extending lengthwise in the first direction in the first surface thereof and being parallel to each other. A plurality of V-grooves also are formed in the second surface so as to extend downwardly from one surface to the other surface such that at an intersection of each of the V-grooves in the first surface and each of the V-grooves in the second surface there is formed an opening that forms a nanopore. In this way a plurality of nanopores are formed in a two-dimensional array in the insulating material at the intersection of each of the plurality of V-grooves in the first surface and the second surface.

In exemplary embodiments, the insulating material layer is formed from a first sub-layer and a second sub-layer that are bonded or secured to each other using any of a number of techniques known to those skilled in the art and appropriate for the materials being used so as to form the insulating material layer. The first sub-layer is configured and arranged so as to include a plurality of V-grooves that extend between opposing surfaces, one of the opposing surfaces comprising the first surface of the insulating material surface. Similarly, the second sub-layer is configured and arranged so as to include a V-groove that extends between opposing surfaces, one of the opposing surfaces comprising the second surface of the insulating material surface. In further embodiments, and as indicated herein the second sub-layer can be configured and arranged so as to include a plurality of grooves that each extend between opposing surfaces, one of the opposing surfaces comprising the second surface of the insulating material surface. When bonded or secured to each other, the first and second-sub-layers are oriented so that the first and second surfaces of the insulating material layer are opposed to each other and so that the V-grooves in the first sub-layer are at an angle with respect to the one or more V-grooves in the second sub-layer, more particularly the first and second sub-layers are oriented so that the V-grooves in the respective sub-layers are orthogonal to each other or at about a 90° angle with respect to each other.

In specific embodiments, at least portions of the tip of each V-groove in the first and second sub-layer is configured and arranged so as to be open and each V-groove is formed in each of the first and second sub-layers so as to be separate from each other. The open portions also are arranged such that at an intersection of each of the V-grooves in the first sub-layer and each of the one or more V-grooves in the second sub-layer there is formed an opening that comprises a nanopore. In this way a plurality of nanopores are formed in a linear or one-dimensional array in the insulating material at the intersection of each of the plurality of V-grooves in the first sub-layer and each V-groove in the second sub-layer.

In an exemplary, illustrative embodiment, the material layer comprises a single silicon wafer and the V-grooves are formed in the silicon wafer using the anisotropic etching property of silicon in KOH solutions. Such a technique allows V-grooves to be formed with high accuracy (e.g., within 20 nm) by controlling the etching rate and etching time. After the V-grooves are etched in the surfaces of the silicon wafers, the assemblage is oxidized to form $SiO_2$ to insulate all silicon surfaces.

In another illustrative embodiment, the material layer comprises two silicon wafers bonded together with pre-etched V-grooves from the opposing sides of the bonded wafer, at an angle around 90° relative to each other. The assemblage is oxidized to form $SiO_2$ to insulate all silicon surfaces.

The present invention also includes a method for reducing the diameters of micropores to nanometer-scale so as to form nanopores using a laser-pulse as a heat source and an electric circuit as a feedback mechanism. This mechanism provides additional control of the pore sizes.

According to one aspect of the present invention, there is featured a device including a member of a solid insulating material, wherein the insulating member is configured and arranged so as to include a through aperture comprising a micropore therein. The micropore is produced when two V-grooves are formed from the opposing sides of the insulating member and the tips of the V-grooves overlap so as to give rise to a micropore. The V-grooves are formed by any of the methods compatible with the base material from which the insulating member is made, including milling, cutting, etching, molding, or extrusion.

According to another embodiment, the space surrounding the micropore is filled with a liquid film of curable polymers. Two crystals that have been cleaved to form atomically sharp edges are placed one on each side of the micropore, supported by the V-groove surfaces. In particular embodiments, the crystal edges cross each other at a predetermined angle, more particularly an angle of about 90°. The crossing edges of the cleaved crystals essentially form or define an area that is small enough that the polymer molecules in the liquid film filling the micropores are displaced. In this way, the molecules of the polymer should be oriented with respect to the cleaved edges and thus forced to make a contour around the crossing point of the crystals. The liquid polymer film is then cured using UV light or heat. In a particular embodiment, the crystals are NaCl crystals which are easily dissolved in water. However, the present invention can be practiced using other crystals known to those skilled in the art and having similar characteristics that lend themselves to being cleaved and being held in a fixed relation while the polymer liquid is cured inside the micropore. After the crystals are removed, a nanopore is formed inside the micropore space.

In an illustrative example of this embodiment, the insulating member is made from plastics such as PMMA (polymethylmethacrylate), or PTFE (polytetrafluoroethylene). The liquid polyimide and NaCl crystals are used to form the nanopore through aperture. This technique yields a nanopore having a length on the order of 1 nm or less, determined by the diameter of the polymer molecule. In the illustrative example, NaCl crystals, common table salt, are cleaved in an environment free of water vapor to form atomically sharp edges. The cleaved crystals are covered with a thin (10 nm) layer of conducting gold and arranged so two such crystal edges are brought together to within a few angstroms distance and held fixed using standard STM electronics and use electron tunneling current as a feedback mechanism. A curable polymer liquid polyimide is then poured into the region of the micropore and cured while the two crystal edges are held fixed. At the crossing point between the two edges, the distance between the edges is so small that no molecules of the polyimide polymer can enter this region. The molecules of the polymer also are advantageously oriented parallel to the respective cleaved edges and be forced to make a contour around the crossing point. Following curing of the polyimide filling the micropore space, the NaCl crystals are removed, e.g., by washing, leaving a nanopore inside the micropore space. In such a methodology, the width and the length of the nanopore are controlled by the distance between the two edges of the crystals, and the diameter of polyimide polymers.

Other objects, features and advantages of the invention shall become apparent as the description thereof proceeds when considered in connection with the accompanying illustrative drawings.

BRIEF DESCRIPTION OF THE DRAWINGS

For a fuller understanding of the nature and desired objects of the present invention, reference is made to the following detailed description taken in conjunction with the accompanying drawing figures wherein like reference character denote corresponding parts throughout the several views and wherein.

DETAILED DESCRIPTION OF THE INVENTION

Figure 1A:
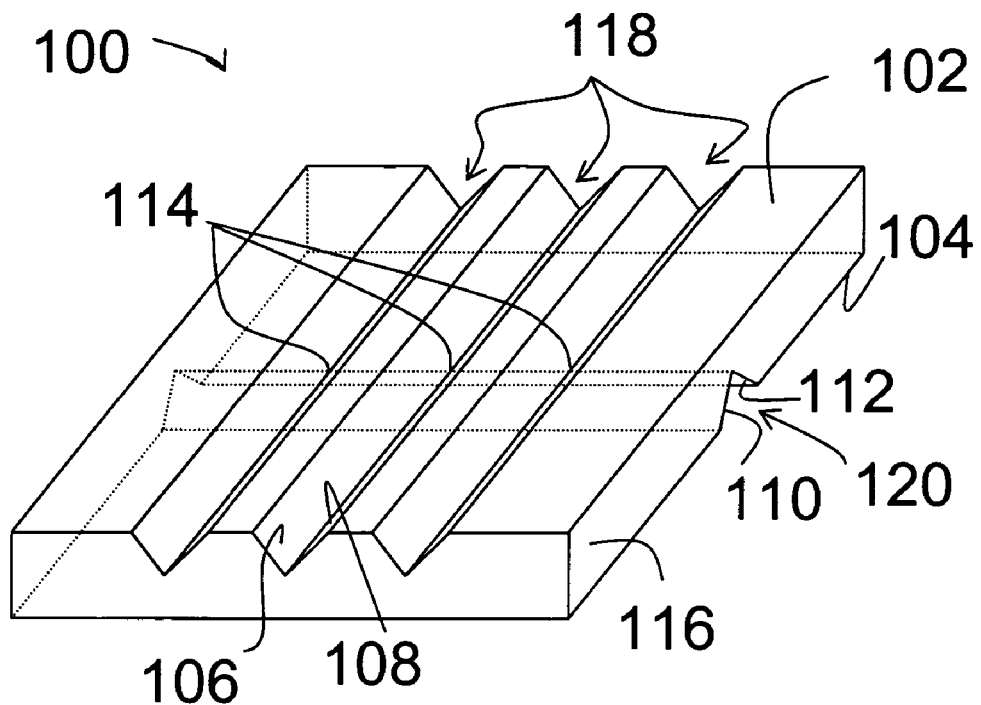
FIG. 1A is a perspective view of an array of electrically-addressable nanopores according to an aspect of the present invention.
Figure 1B:
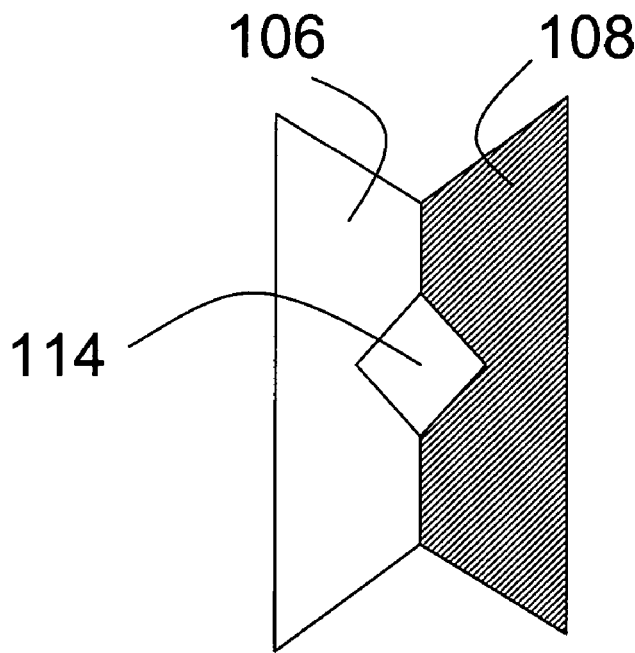
FIG. 1B is a detailed plan view of one nanopore of the present invention.

Referring now to the drawings, a preferred embodiment of the present invention is illustrated in FIG. 1A and FIG. 1B. In FIG. 1A, there is shown a perspective view of device 100 including an array of electrically-addressable nanopores 114, more particularly a linear array of nanopores. The device 100 includes an insulating member 116 having a top surface 102 and a bottom surface 104. A plurality of grooves 118 are formed in the top surface using any of a number of techniques known to those skilled in the art that are appropriate for the material comprising the insulating member. The V-grooves 118 in the top surface 102 are formed in the insulating member 116 so as to generally extend downwardly towards the bottom surface 104 a predetermined distance from the top surface 102. Correspondingly, the V-groove 120 in the bottom surface 104 is formed in the insulating member 116 so as to generally extend upwardly towards the top surface 102 a predetermined distance from the bottom surface.

In addition, at the points of intersection between the V-grooves 118 in the top surface 102 and the V-groove 120 in the bottom surface 104, the insulating member is configured and arranged so an opening or nanopore 114 is provided in the insulating member 116 so as to allow ions to flow from each of the top surface V-grooves 118 to the bottom surface groove 120, and vice versa, when surfaces 102 and 104 are each sealed with additional insulating members. The formation of the V-grooves 118, 120 and the nanopores 114 are discussed in more detail hereinafter.

In the preferred embodiment, the insulating member 116 is single-crystal silicon wherein the surfaces are oxidized after the fabrication of the V-grooves and the nanopores. On top surface 102 a set of parallel V-grooves are etched using KOH or TMAH (tetramethylammonium hydroxide) with proper additives and procedures known in the art. On the bottom surface 104, a single V-groove is etched in the direction perpendicular to the V-grooves on the top surface 102. The nanopores 114 are formed in the insulating member using any of a number of techniques appropriate for the material being used and appropriate for forming a nanopore having the desired width and length for e.g., rapidly characterizing biomolecules. In one particular embodiment, the nanopores 114 are formed at the intersections of the top and bottom surface V-grooves 118, 120. In another particular embodiment, portions of the tips of the top and bottom surface V-grooves 118, 120 are formed so as to included an opening in each groove proximal the point of intersection such that the sharp edge openings in the grooves are aligned so as to form a nanopore.

In addition, in the illustrated embodiment, the V-grooves 118, 120 formed in the top and bottom surfaces 102, 104 so as to provide deep V-shaped grooves. While V-shaped grooves are shown, this shall not be limiting as other shapes as are known to those skilled in the art that are otherwise adaptable and consistent with the function of the V-grooves in the present invention and are contemplated for use in the present invention.

In a particularly illustrative embodiment, the insulating member 116 is subsequently oxidized after further processing of the insulating member to form $SiO_2$, an insulating material. Although, the starting material is silicon, this shall not be considered limiting as other materials are contemplated for use with the present invention that would allow creation of the linear array of nanopores 114 as herein described using techniques that are appropriate for the material of use.

More specifically, the silicon material is subjected to micromachining techniques are known to those skilled in the art to form the V-grooves 118, 120 and the nanopores 114. In particular, the V-grooves and the nanopores are etched in the silicon wafer using an oxide or nitride mask, in KOH solutions with relatively high accuracy, or by use of electron-beam beam lithography and wet etching techniques. Alternately, during the formation of the V-grooves 118, 120, portions of the tips or valleys of the grooves, in particular the portions proximal the intersections of the top and bottom surface grooves, are further etched so as to form an opening in these portions of the tips. In this way, "cutting-edges" pores are yielded, one by directly etching from one or both sides of the silicon wafers with grooves at 90° relative to each other, and the other by bonding two silicon wafers with the sharp edges of the V-grooves facing each other at 90°. As is known to those skilled in the art, the etching of the surfaces can be accurately controlled by controlling the etching rate and etching time. The etching process can be actively stopped using any of the feedback mechanisms known in the art. Following such etching, the assemblage is then oxidized to form silicon oxide to insulate all silicon surfaces, thereby forming the insulating member in its operable form.

Figure 2:
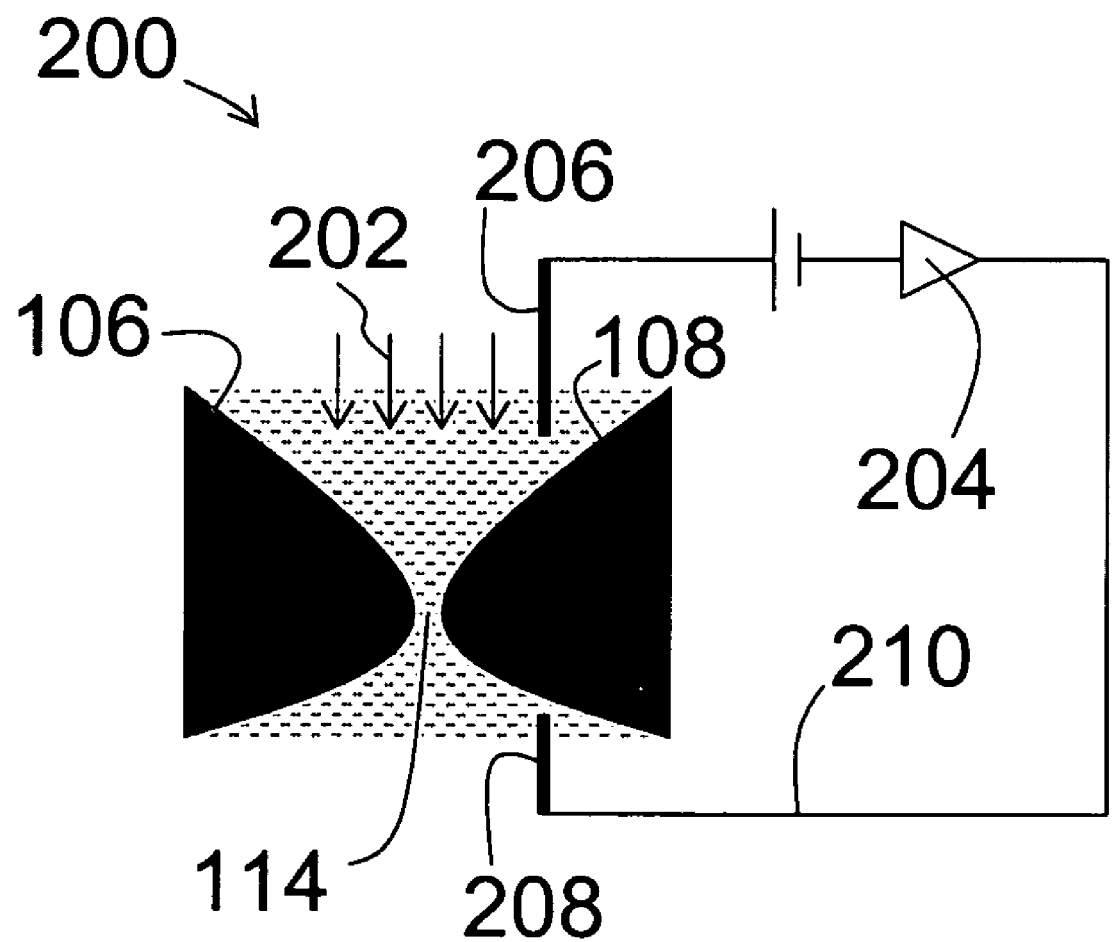
FIG. 2 is a schematic view of an exemplary electrical-feedback mechanism for controlling the size of the nanopores using pulsed-laser heating.

Now referring to FIG. 2, after making the insulating member 116 so as to be in its operable form, the nanopores 114 are further examined using, for example, an electron microscope to determine if the nanopores that are formed have the desired width. If the as-etched nanopores are larger than 10 nm where a 2-5 nm pore size is desired, the present invention provides a method for modification of the pore size. The nanopore 114 is exposed to a high-energy laser beam 202 to reduce the dimensions of the nanopore 114. As more fully describe below, small holes shrink spontaneously due to surface tension when the $SiO_2$ is fluidized by the laser beam 202 and when the laser beam 202 is switched off, the $SiO_2$ material near 114 quenches and retains its shape.

It is known in the art to use a beam of high-energy electrons to heat up and to modify the dimensions of the $SiO_2$ nanopores in a controlled fashion (Storm et al.). It has been found that an electron intensity around $10^6$ to $10^7$ $A/m^2$ causes pores to shrink if the pore had an initial diameter about 50 nm or lower. The following further illustrates this modification process using for example, short light pulses from a laser of proper wavelength and intensity. Accordingly, in the present invention, the heating mechanism is a laser pulse 202 and the feedback mechanism is an electric circuit comprising of electrodes 206, 208, wiring 210, current amplifier 204, and a battery. Using laser beams instead of electron beams can greatly reduce cost of fabrication for large number of pores. The power of this technique lies in the possibility to fine-tune the diameter of nanopores with great precision. By lowering the laser beam intensity or blanking it, the shrinking process can be stopped within seconds when the desired diameter has been reached. In addition, changes in pore diameter can be monitored in real time using the ionic current through the pore. As such, the use of this modification technique provides a mechanism to reduce the required dimensional control in the lithographic process for forming nanopores from crossing V-grooves, because any pore with a diameter below 50 nm can be shrunk to a nanometer-sized pore as known in the prior art (Storm et al.).

The physics attendant with the growing and shrinking that has been observed using the electron-beam process is determined by the surface tension of the viscous silicon oxide. The same physics should apply to laser-heating cases. In this state, the structure will deform to find a configuration with a lower free energy. Simple free-energy consideration suggests that the surface energy of pores with radius $r<\frac{1}{2}h$ can be lowered by reducing $r$, and that the surface energy for pores with radius $r>\frac{1}{2}h$ can be increased by increasing size. The "critical diameter" discriminating the two cases is of order of the thickness of the $SiO_2$ near the pore, with the exact ratio depending on the geometry of the pore. This scaling argument is valid at any scale, as has been proven by Storm et al.

Figure 3A:
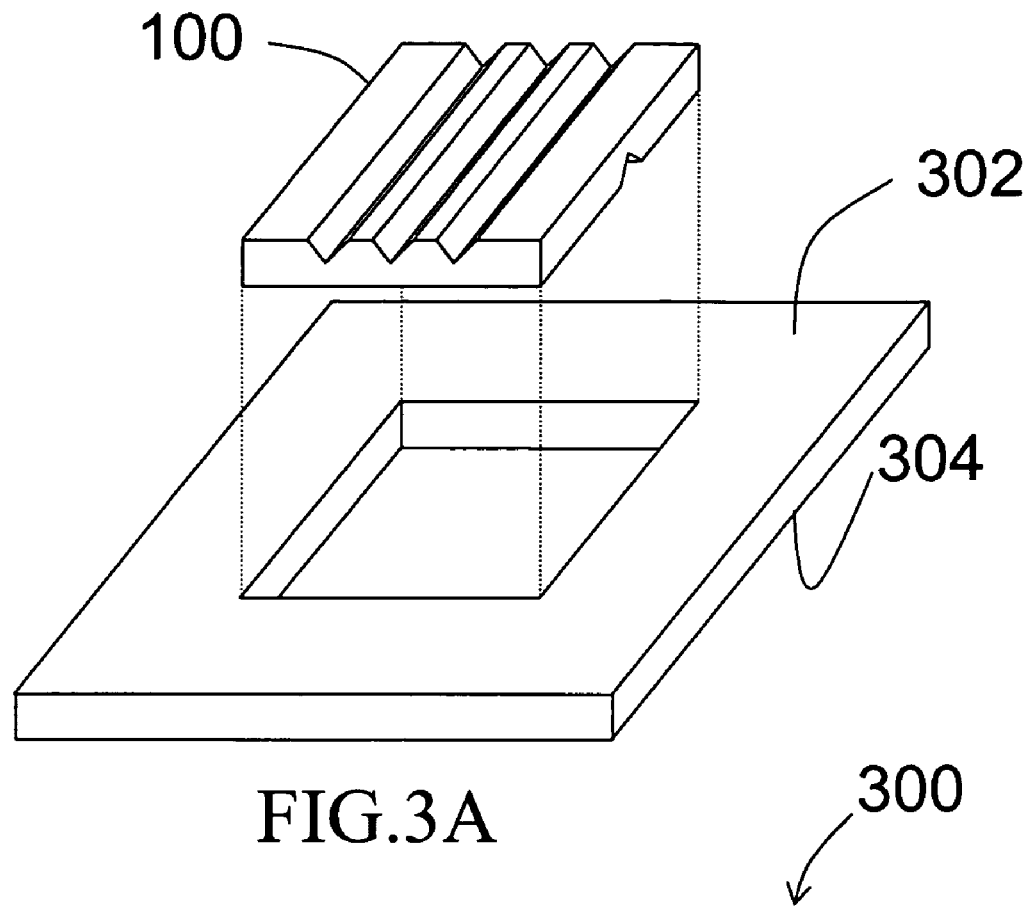
FIGS. 3A and 3B show a method of incorporating an electrically-addressable-nanopore-array device into a holding chip.
Figure 3B:
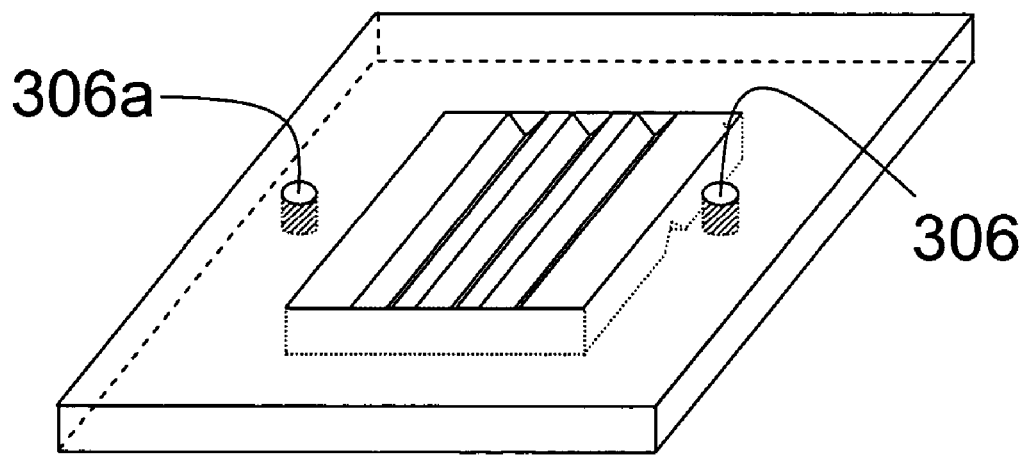

Referring now to FIG. 3A and FIG. 3B, the addressable-nanopores device 100 is assembled in another insulating member with first surface 302 and second surface 304 using any of the methods known in the art. The integrated device is now named 300. For silicon processing, 300 is a single piece of silicon crystal as the starting material. Holes 306 and 306a are machined as throughputs for fluid control.

Figure 4:
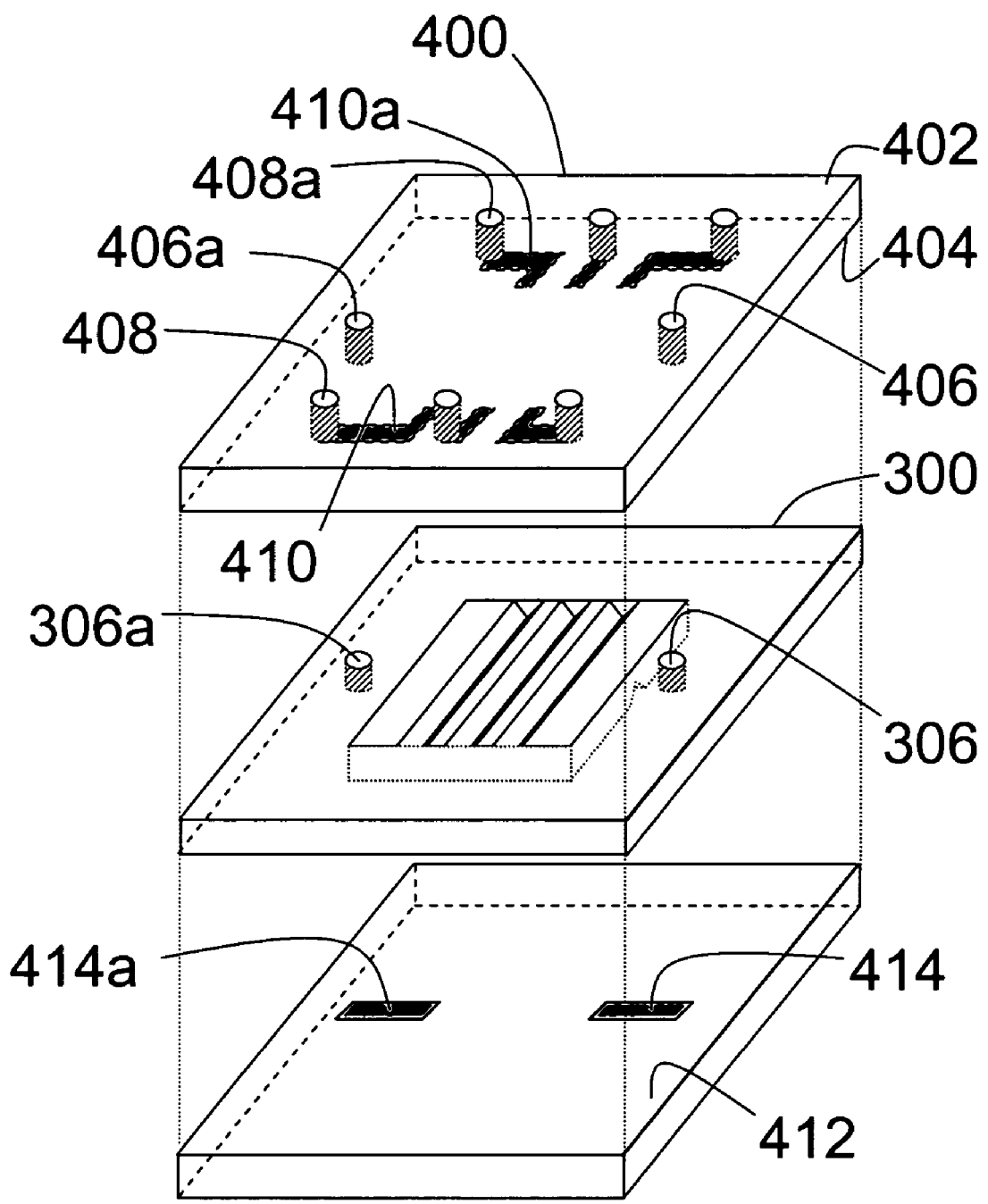
FIG. 4 is a perspective view illustrating one of the methods for assembling a microfluidic-nanofluidic system incorporating the addressable-nanopore arrays of the present invention.

Referring now to FIG. 4 there is shown a schematic view of an integrated electrically-addressable-nanopore-array according to the present invention configured with microfluidic platform 400, and base platform 412. 400 and 412 are insulating materials. An electrically-addressable-nanopore-array system according to the present invention includes top platform 400 and bottom platform 412, made from machined plastics or cured polymeric matter such as PDMS as are known to those skilled in the art, which seal the top and bottom surfaces of the array 300 using proper sealant known in the art. Following fabrication of the electrically-addressable-nanopore-array 100, the top platform 400 is secured or bonded to the top surface of 300 thereof using any of a number of techniques known to those skilled in the art appropriate for the materials being used. The bottom platform 412 is secured or bonded to the bottom surface of 300 thereof using any of a number of techniques known to those skilled in the art appropriate for the materials being used This is preferably done after the electrically-addressable-nanopore-array 100 is determined to be in operable condition (e.g., nanopores of the desired width and length appropriate for the intended applications). In addition, the device 300 is appropriately aligned with shallow trenches 410 and 410a on the bottom surface 404 of the top platform 400 as fluid-flow channels connecting the top V-grooves in device 300. Electrodes (e.g., Ag/AgCl wires) are then connected to the ports on the top platform 400. As is known to those skilled in the art other devices, apparatuses and systems (not shown) are interconnected to the electrically-addressable nanopore array device 300 for purposes of supplying samples for analysis, for collection of data and for the analysis of the collected data.

In the assembly shown in FIG. 4, the fluid sample flows in from port 406, through hole 306 and shallow trench 414 (on platform 412), entering V-groove 120 and exiting from shallow trench 414a, through hole 306a, out of port 406a. Similarly, one can flush fluids through the top V-grooves 118 on device 300. When a voltage is applied between 406 and 408, DNA or RNA molecules can flow through the nanopore defined by two crossing V-grooves, and their movement is recorded as reduction of the ionic current in the corresponding nanopore as known in the art.

The unique geometry of this invention also provides a mechanism for removing dust or impurity particles blocking the pore. In the event a particle is immobile near the pore, it can be removed by flushing the fluid flow in the corresponding V-groove.

Figure 5A:
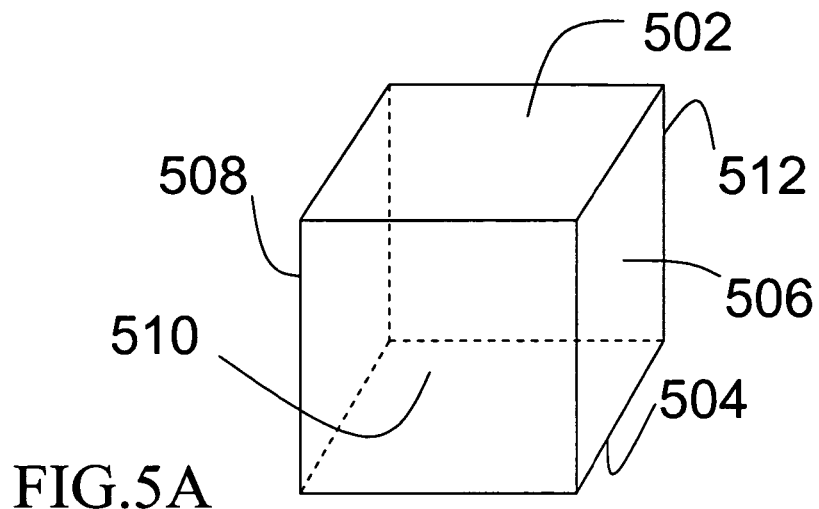
FIGS. 5A, 5B and 5C show the steps for a procedure for fabricating an aperture of micrometer-scale in a solid medium using a V-groove cutting mechanism.
Figure 5B:
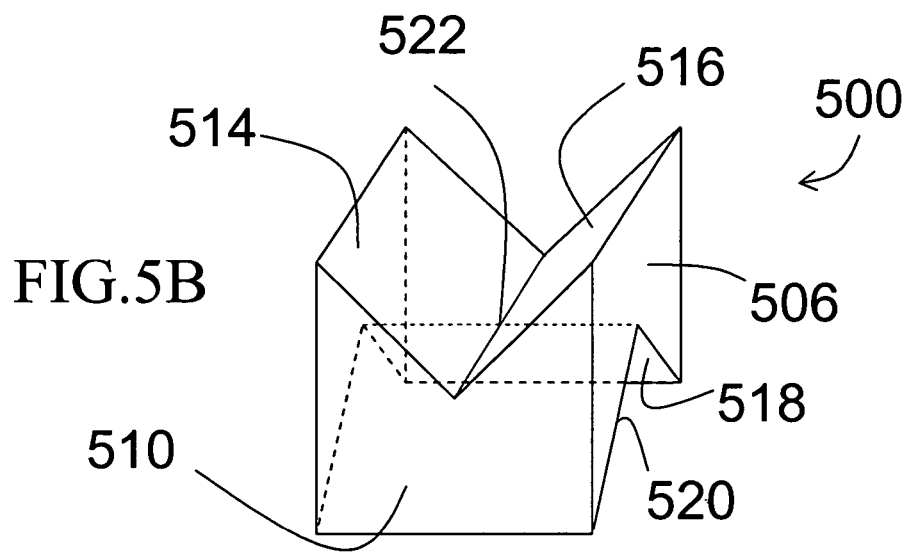
Figure 5C:
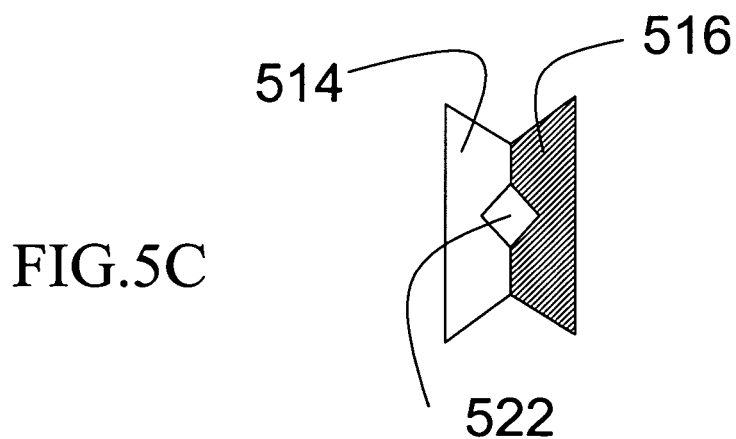
Figure 6:
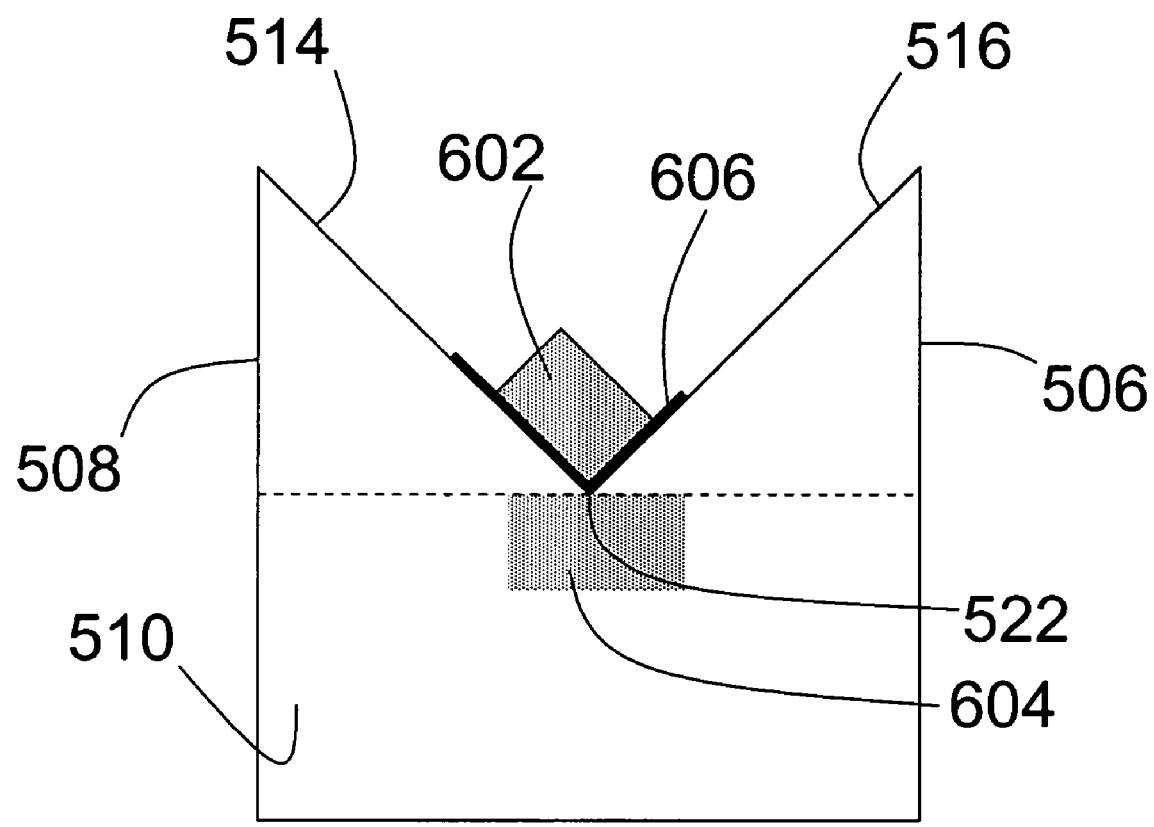
FIG. 6 is a front view of an alternate procedure forming a nanopore inside the micrometer-sized aperture formed in the procedure of FIG. 5.
Figure 7:
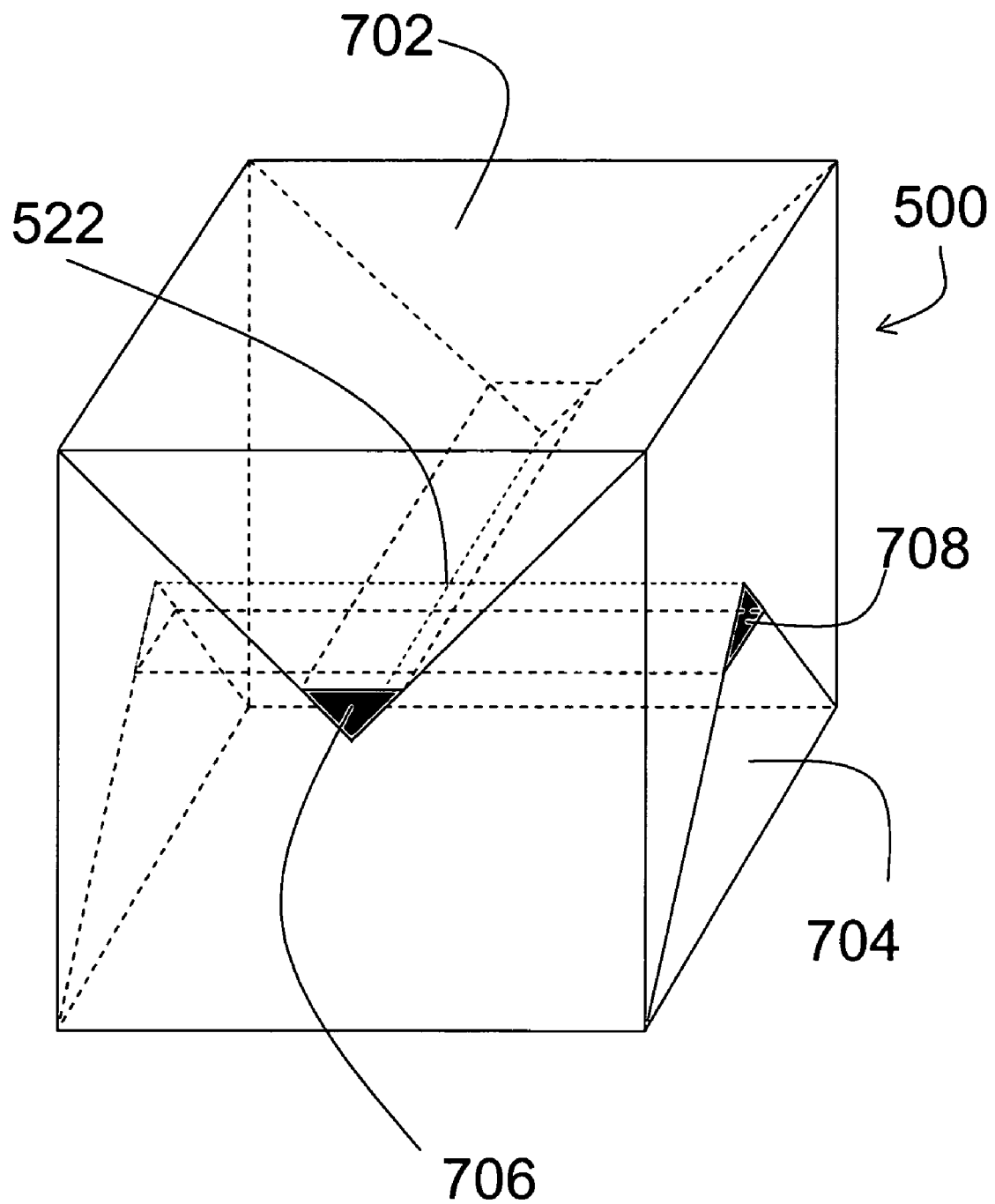
FIG. 7 is a perspective view of two V-shaped microfluidic channels coupled through a nanopore (formed inside a micropore).

Referring now to FIGS. 5-7, various views are shown to illustrate the process for making a nanopore in an insulating member 500 that includes a micropore 522 according to one aspect of the present invention. More particularly, FIG. 5 is a diagrammatic view illustrating the cutting-V-grooves mechanism for forming the micropore 522 of an insulating member 500 of the present invention using hard plastics or other insulating media.

The following describes one technique for making the insulating member 500 of the present invention. Starting with a block of solid media (such as machinable plastics) of the shaped of a cube, a deep V-shaped groove is cut from the side 502. Another V-shaped groove is cut from the side of 504. The two V-grooves are oriented perpendicular to each other. The cutting can be by machining or molding. The V-grooves are cut such that a micropore 522 is open. The next step is to reduce the micropore 522 to a nanopore using another embodiment of the present invention. In a special embodiment, a thin layer of curable polymer in the liquid form is spread on surfaces 514 and 516, and filling the micropore 522. Next a NaCl crystal coated with gold is placed with its sharp edge facing the micropore 522. Another NaCl crystal with surface coated with a layer of gold is placed between the V-groove surfaces 518, 520 with its sharp edge facing the micropore 522. The two NaCl crystals are slowly pushed against each other so as to squeeze out the polymers in the touch point of the two edges. In a special embodiment, the distance between the two edges is controlled by STM electronics known to those skilled in the art. The distance between the cutting edges is fixed while the polymer is cured (by using UV light or heat). After curing the polymer, the NaCl crystals are removed by washing, leaving a nanopore formed inside the micropore 522. However, other methods or techniques are contemplated that are adaptable to maintain crystals in fixed relation so as to provide a mechanism for defining a through aperture that comprises a nanopore. Such a methodology advantageously yields an insulating member having a nanopore whose length can be controlled so as to be less than 10 nm, particularly about 1 nm or less, more particularly about 0.5 nm. As indicated herein, conventional techniques for forming nanopores for such use, result in a structure in which the nanopore has a length in excess of the spacing (about 0.5 nm) between two adjacent nucleotides to be characterized which can lead to inaccuracies in the characterization.

As illustration of this technique, NaCl crystals are cleaved in an environment free of water vapor to form atomically sharp edges and two of these cleaved crystals are brought together within a few angstroms distance of each other. In addition, the crystals are arranged so the crystal edges are cutting each other at an angle of about 90°, as shown in the diagram in FIG. 6. The two crystals are held in fixed relation using standard STM electronics (not shown) and using the electron tunneling current as a feedback mechanism. At the crossing point between the two edges, the distance between the edges is so small that no polymer molecules larger than a certain size can enter into this region. Stated another way, the crossing point is established such that molecules having a width greater than a desired width cannot enter into this region. The crystals contemplated for use in the present invention include a wide range of crystals and in a particular, exemplary illustrative embodiment the crystals include NaCl and GaAs crystals.

The crystals when so arranged use the crystal edges as a mold. After arranging the crystals in fixed relation to one another, an insulating material, such as a curable polymer liquid polyimide, is poured into the region of the cutting edges and allowed to cure while the two crystal edges are held fixed. The distance between the edges is set to be so small that no polyimide molecules can enter this forbidden region. The polyimide molecules are expected to be advantageously oriented parallel to the respective cleaved edges and are forced to make a contour around the crossing point, leaving a small hole of a given width and length. The width and the length of the small hole are controlled by the distance between the two edges and the diameter of the polyimide molecule.

In further processing, after the insulating member 500 is so-formed, the crystals that were used to controllably form the nanopore or opening in the insulating member are removed using any of a number of techniques known to those skilled in the art that do not appreciably effect the insulating material about the formed hole, e.g., in the case of NaCl crystals, by washing with water. Following removal of the crystals, an opening is formed in the member such as that illustrated in FIG. 5, having a desired width and length. Because the chemical groups (nucleotides) of a DNA molecule have slightly different sizes, one can identify the nucleotides of a DNA molecule, and hence sequence the DNA molecule, by measuring the time dependence of the nanopore conductance. In this way, a nanopore is formed in the insulating material; having a desired width and length for purposes of characterizing the biomolecules, more particularly fast characterization of the biomolecule. Such an insulating member 500 is thus of great utility for a wide range of uses including forensics, rapid sequencing of DNA and research. As indicated herein, the amount of the conductance drop will be a measure of the physical size of the part of the DNA molecule that is inside the narrowest part of the channel.

In an alternative embodiment, referring now to FIG. 7, the V-shaped cutouts from the insulating member 500 are refilled except leaving two small V-shaped channels 706 and 708 meeting at the nanopore inside the micropore 522. The V-grooves 706, 708 can be used to push the fluid through these channels while monitoring the molecules using the nanopore connecting the two V-groove channels using the standard patch-clamp electronics known to those skill in the art.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed:

1. A process to fabricate nanopores and micropores, comprising the steps of:
   providing an integral substrate member having a thickness and first and second opposing surfaces;
   forming at least one first V-shaped channel lengthwise in a first direction in said first surface; and
   forming at least one second V-shaped channel lengthwise in a second direction in said second surface, said second direction being disposed at an angle relative to said first direction,
   wherein said first channel and said second channel extend inwardly from said first and second surfaces and intersect at a point, said point defining a pore extending through said substrate member from said first surface to said second surface;
   placing a first crystal into said first channel adjacent said pore;
   placing a second crystal into said second channel adjacent said pore;
   applying a force to urge said first and second crystals towards one another to maintain their position relative to one another;
   placing an uncured liquid polymer material into said first and second channels adjacent said first and second crystals;
   curing said polymer material to provide a plurality of polymer molecules, the polymer molecules each having a diameter; and
   removing said crystals from said pore, said pore now having a size defined by the point of intersection between said first and second crystals and the diameter of one of said plurality of polymer molecules.

2. The process of claim 1, said step of forming at least one second V-shaped channel in said second surface further comprising:
   forming a plurality of parallel V-shaped channels in said second surface, wherein said first V-shaped channel and said plurality of second V-shaped channels intersect at an array of points defining an array of pores extending through said substrate member from said first surface to said second surface.

3. The process of claim 1, said step of forming at least one first V-shaped channel in said first surface further comprising:
   forming a plurality of parallel V-shaped channels in said first surface wherein said second V-shaped channel and said plurality of first V-shaped channels intersect at an array of points defining an array of pores extending through said substrate member from said first surface to said second surface.

4. The process of claim 3, said step of forming at least one second V-shaped channel in said second surface further comprising:
   forming a plurality of parallel V-shaped channels in said second surface, wherein said plurality of first v-shaped channels and said plurality of second V-shaped channels intersect at an array of points defining an array of pores extending through said substrate member from said first surface to said second surface.

5. The process of claim 1, wherein said substrate member is selected from the group consisting of: silicon, hard plastics and PTFE.

6. The process of claim 1, wherein said substrate member has a surface layer selected from the group consisting of: silicon oxide, silicon nitride, polyimide, PMMA and PTFE.

7. The process of claim 1, wherein the method used in said steps of forming said first and second channels is selected from the group consisting of: etching, milling, cutting, molding and extrusion.

8. The process of claim 1, wherein said pore has a width that is between about 1 nm and 100 μm.

9. The process of claim 1, wherein said pore is electrically addressable.

10. The process of claim 2, wherein said array of pores are individually electrically addressable.

11. The process of claim 3, wherein said array of pores are individually electrically addressable.

12. The process of claim 1, wherein said crystals are sodium chloride.

13. The process of claim 12, wherein said sodium chloride crystals are coated with a thin layer of electrically conductive material.

14. The process of claim 12, wherein said step of removing said crystals is dissolving said crystals.

* * * * *